(12) United States Patent
Chuck

(10) Patent No.: US 7,067,673 B2
(45) Date of Patent: Jun. 27, 2006

(54) PROCESS AND CATALYST FOR THE PREPARATION OF ACETYLPYRIDINES

(75) Inventor: Roderick John Chuck, Brig-Glis (CH)

(73) Assignee: Lonza AG, Basel (CH)

(*) Notice: Subject to any disclaimer, the term of this patent is extended or adjusted under 35 U.S.C. 154(b) by 367 days.

(21) Appl. No.: 10/467,381

(22) PCT Filed: Feb. 14, 2002

(86) PCT No.: PCT/EP02/01533

§ 371 (c)(1),
(2), (4) Date: Aug. 7, 2003

(87) PCT Pub. No.: WO02/066433

PCT Pub. Date: Aug. 29, 2002

(65) Prior Publication Data

US 2004/0073040 A1    Apr. 15, 2004

Related U.S. Application Data

(60) Provisional application No. 60/332,546, filed on Nov. 26, 2001.

(30) Foreign Application Priority Data

Feb. 19, 2001 (EP) .................................. 01103953

(51) Int. Cl.
*C07D 213/60* (2006.01)

(52) U.S. Cl. ...................................... 546/314; 546/315
(58) Field of Classification Search .................... None
See application file for complete search history.

(56) References Cited

U.S. PATENT DOCUMENTS 3,979,400 A * 9/1976 Rieger et al. ............... 546/314
4,950,763 A * 8/1990 Schommer et al. .......... 546/314

FOREIGN PATENT DOCUMENTS

| EP | 0352674 | 1/1990 |
| GB | 1249079 | 10/1971 |
| WO | 98/50374 | 11/1998 |

OTHER PUBLICATIONS

International Search Report for applicants corresponding International patent application.
Girardon, Marc, et al., Journal of Organic Chemistry, vol. 63, No. 26, (1998), pp. 10063-10068.
Houben-Weyl, vol. VII/2a, pp. 632-633.

* cited by examiner

*Primary Examiner*—Kamal A. Saeed
*Assistant Examiner*—Nyeemah Grazier
(74) *Attorney, Agent, or Firm*—Fisher, Christen & Sabol

(57) ABSTRACT

A process for the production of acetylopyridines of the formula (1):

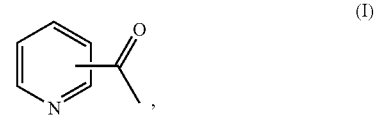

(I)

by reacting a pyridinecarboxylic ester of the formula (II):

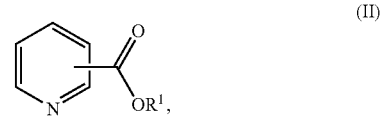

(II)

wherein $R^1$ is $C_{1-6}$-alkyl, with acetic acid in the gas phase in the presence of a catalyst. The active material of the catalyst is titanium dioxide and at least one alkali or alkaline earth metal oxide, and it is supported on an alumina-silica support having an apparent porosity of at least 50 percent. The process has the advantage of producing only small amounts of by-products (e.g, pyidine).

18 Claims, No Drawings

PROCESS AND CATALYST FOR THE PREPARATION OF ACETYLPYRIDINES

This is a 371 U.S. national stage application of International (PCT) Patent Application PCT/EP02/01533, filed on Feb. 14, 2002, that has priority benefit of U.S. Provisional Application Ser. No. 60/332,546, filed on Nov. 26, 2001, and that has priority benefit of European Patent Application No. 01103953.4, filed on Feb. 19, 2001.

The invention relates to a process for the production of acetylpyridines of formula

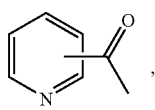

(I)

in particular 3-acetylpyridine. It further relates to a catalyst suitable for the process of the invention.

3-Acetylpyridine is assuming increasing importance in the pharmaceutical and fine chemical industry as an intermediate and a building block. Up to the present, 3-acetylpyridine has been prepared using often multistage processes starting from nicotinic acid, or from other starting materials which are not readily available (for example 3-ethylpyridine). Instead of using a heteroaromatic acid, it is possible to use derivatives. This is particularly useful when the acid is non-volatile and/or has a tendency to decompose at higher temperatures. Thus ethyl nicotinate was condensed with acetic acid at 520° C. to give 37% yield of 3-acetylpyridine (Houben-Weyl, Vol. VI/2a, pp. 632–633).

Recently a process for the production of 3-acetylpyridine has been described in EP-A-0 352 674, which utilises a catalyst based on titanium dioxide and an alkali or alkaline earth metal oxide or hydroxide. Using the methyl ester of nicotinic acid and acetic acid and a catalyst composed of 98% titanium dioxide (as anatase) and 2% sodium oxide, selectivities between 54% and 60% were reported. Pyridine was produced as a side product through decarboxylation of the nicotinate in amounts between 29 and 41%. Various other methods have been described which do not lead to satisfactory results (cf. EP-A-0 352 674).

The purpose of the present invention is to improve the selectivity of the state-of-the-art processes for 3-acetylpyridine, thus avoiding or reducing the losses caused by the formation of large quantities of unwanted side-products.

According to the invention, this has been accomplished by the process of the invention.

It has been found that in the gas-phase reaction of pyridinecarboxylic esters of formula

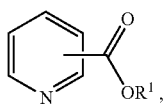

(II)

wherein $R^1$ is $C_{1-6}$-alky, with acetic acid to give acetylpyridines (I) the selectivity of the titanium dioxide-based catalysts of EP-A-0 352 674 can be substantially improved by employing a high-porosity alumina-silica support having an apparent porosity of at least 50%, as determined by the Archimedes method.

Preferably, the process according to the invention is carried out with a $C_{1-6}$-alkyl nicotinate as starting material to give 3-acetylpyridine.

It has further been found that by employing higher boiling pyridinecarboxylic esters (II) the ease of separation of the reaction products can be increased. Lower esters of e.g. nicotinic acid have boiling points similar to those of the desired product, which results in separation difficulties in distillation if the conversion is less than 100%. Use of higher boiling (and more stable) esters largely avoids this problem. Examples of this are the butyl, pentyl or hexyl (including the isomers such as isobutyl, sec-butyl, isopentyl etc.) esters of nicotinic acid instead of methyl, ethyl or propyl esters, whose boiling points at atmospheric pressure differ only by 3–4 K (ethyl) and 15–16 K (methyl and propyl), respectively, from that of 3-acetylpyridine. The difference in boiling point between butyl nicotinate and 3-acetylpyridine at atmospheric pressure is 32 K.

Preferably, pyridine carboxylic esters (II) having a boiling point (at atmospheric pressure) exceeding that of the product acetylpyridine (I) by more than 20 K are used as starting materials.

The preferred reaction temperature is 350 to 450° C.

Advantageously, the reaction is carried out in the presence of water and using an excess of acetic acid.

The weight ratio of alumina to silica in the catalyst support is advantageously between 70:30 and 90:10, preferably between 75:25 and 85:15.

Preferably, the apparent porosity of the catalyst support is between 60 and 70%.

The packing density of the catalyst support is preferably lower than 1000 kg/m³, more preferably between 600 and 800 kg/m³.

Preferably, the titanium dioxide content of the catalyst is 5 to 20 wt. percent, based on the weight of the support.

The catalyst may be prepared by a process comprising the steps of (i) impregnating an alumina-silica support having an apparent porosity of at least 50% with a solution of titanium tetrachloride in aqueous hydrochloric acid to obtain a first catalyst precursor, (ii) drying, (iii) calcining, (iv) impregnating the calcined first catalyst precursor with a solution or suspension of a hydroxide and/or oxide of an alkali metal and/or alkaline earth metal to obtain a second catalyst precursor, (v) drying and (vi) calcining the dried second catalyst precursor to obtain the final catalyst.

The impregnation of the support is not limited to the use of titanium tetrachloride. Thus either other soluble salts of titanium, or even a finely-divided slurry of titanium oxide can be used. It is also possible to replace the hydroxides or oxides of alkali or alkaline earth metals by suitable precursors, e.g. salts of said metals which decompose on heating.

Advantageously, the ratio of alumina to silica in the support is between 70:30 and 90:10, preferably between 75:25 and 85:15.

The apparent porosity of the catalyst support is preferably between 60 and 70%.

Preferably, the titanium dioxide content of the catalyst is 5 to 20 wt. percent, based on the weight of the support.

The following non-limiting examples will illustrate the process of the invention and the preparation of the catalyst of the invention.

EXAMPLE 1

Preparation of Catalyst:

For the preparation of the catalyst porous silica-alumina spheres are utilised as a support A suitable material is supplied by the Norton Chemical Process Products Corporation of Akron, Ohio with the following typical specification:

| | |
|---|---|
| Size and Shape: | 4 mm Ø spheres |
| Surface Area: | 12 m$^2$/g |
| Apparent Porosity: | 65% |
| Packing Density: | 710 kg/m$^3$ |
| Total Pore Volume (by Hg porosimetry): | 0.5 ml/g |
| Al$_2$O$_3$: | 79–81% |
| SiO$_2$: | 17–19% |

An aqueous solution of titanium tetrachloride (22% expressed as TiO$_2$, 0.21 mol, 16 g) was prepared by adding 23 ml (40 g, 0.21 mol) of TiCl$_4$ to a of 15 ml of concentrated hydrochloric acid and 60 ml of demineralised water. The final solution was stirred for several minutes and cooled down.

The above silica-alumina spheres (250 g) were impregnated in a rotating glass vessel or metal drum using the wet incipient technique by spraying the TiCl$_4$ solution at 25–30° C. The catalyst precursor was subsequently dried under vacuum (bath temperature: 90–95° C.) for 1 h, then at 120° C. for 12 h and finally calcined at 400° C. for 12 h under a stream of air (500 ml/min). An analysis gave 7% Ti.

The calcined spheres were again placed in a rotating drum and sprayed with dilute sodium hydroxide solution (1.5 g NaOH as a 5% aqueous solution).

The catalyst was dried at 120° C. for 12 h and then calcined for 1 h at 500° C.

EXAMPLE 2

Preparation of 3-acetylpyridine

An electrically heated tubular reactor with an inner diameter (i. d.) of 12 mm was filled with 15 ml (12 g) of catalyst from example 1. Over a period of 12 h, a mixture of 17.9 g butyl nicotinate, 32 g water and 125 g acetic acid was metered using a precision pump to the reactor operating at 410° C. From the reaction mixture, 8.9 g of 3-acetylpyridine, 0.9 g of pyridine and 1.3 g of butyl nicotinate were obtained. This corresponded to a yield of 73% 3-acetylpyridine at a butyl nicotinate conversion of 93% (selectivity 78%). The selectivity of pyridine formation was 11%.

COMPARATIVE EXAMPLE 1

Preparation of 3-acetylpyridine Using Catalyst Described in EP-A-0 352 674

An electrically heated tubular reactor with an i. d. of 12 mm was filled with 15 ml (≈15 g) of catalyst prepared according to EP-A-0 352 674, example 1. Over a period of 60 h, a mixture of methyl nicotinate (78 g), water (149 g) and acetic acid (523 g) was metered using a precision pump to the reactor operating at 410° C. From the reaction mixture, 30.5 g of 3-acetylpyridine, 8.5 g of pyridine and 9.0 g of methyl nicotinate were obtained. This corresponded to a yield of 45% 3-acetylpyridine at a methyl nicotinate conversion of 88% (selectivity 50%). The selectivity of pyridine formation was 19%.

COMPARATIVE EXAMPLE 2

Preparation of 3-acetylpyridine Using Catalyst Described in EP-A-0 352 674

An electrically heated tubular reactor with an i. d. of 12 mm was filled with 15 ml (≈15 g) of catalyst prepared according to EP-A-0 352 674, example 1. Over a period of 63 h, a mixture of butyl nicotinate (104 g), water (162 g) and acetic acid (606 g) was metered using a precision pump to the reactor operating at 405° C. From the reaction mixture, 30 g of acetyl pyridine, 3 g of pyridine and 26 g of butyl nicotinate were obtained. This corresponded to a yield of 43% 3-acetylpyridine at a butyl nicotinate conversion of 75% (selectivity 58%). The selectivity of pyridine formation was 5%.

EXAMPLE 3

Preparation of 3-acetylpyridine

A tubular reactor with an i. d. of 23.5 mm was filled with 270 ml (≈227 g) of catalyst from example 1. A mixture of butyl nicotinate (30 g/h), water (54 g/h) and acetic acid (210 g/h) was fed over an evaporator using a metering pump to the tubular reactor heated by a salt bath. A small flow of nitrogen (1 l/h) guaranteed the transport of the vapours. The temperature of the bath was 410° C. The reaction vapours were condensed in an aqueous circulation system. After a total running time of 35 h, the reaction solution was collected. A portion of this solution corresponding to a total of 710 g of butyl nicotinate was worked up to isolate the product. 81% of butyl nicotinate was converted to give 293 g of 3-acetyl-pyridine, corresponding to a selectivity of 75% and a yield of 61%. The selectivity of pyridine formation was 4%.

The invention claimed is:

1. A process for the preparation of an acetylpyridine of the formula:

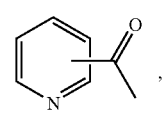

(I)

comprising reacting a pyridinecarboxylic ester of the formula:

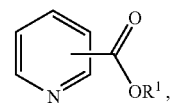

(II)

where R$^1$ is C$_{1-6}$-alkyl, with acetic acid in the gas phase in the presence of a catalyst whose active material comprises titanium dioxide and at least one alkali or alkaline earth metal oxide, wherein the catalyst comprises an alumina-silica support having an apparent porosity of at least 50 percent.

2. The process of claim 1, wherein the acetylpyridine (I) prepared is 3-acetylpyridine and the pyridinecarboxylic ester (II) is a C$_{1-6}$-alkyl nicotinate.

3. The process of claim 2, wherein the pyridinecarboxylix ester (II) has a boiling point at atmospheric pressure that is more than is more than 20° K.

4. The process of claim 3, wherein the reaction temperature is between 350 and 450° C.

5. The process of claim 4, wherein the weight ratio of alumina to silica in the catalyst support is between 70:30 and 90:10.

6. The process of claim 5, wherein the apparent porosity of the catalyst support is between 60 and 70 percent.

7. The process of claim 6, wherein the packing density of the catalyst support is between 600 and 1000 kg/m$^3$.

8. The process of claim 7, wherein the titanium dioxide content of the catalyst is 5 to 20 wt. percent, based on the weight of the support.

9. The process of claim 4, wherein the weight ratio of alumina to silica in the catalyst support is between 75:25 and 85:15.

10. The process of claim 6, wherein the packing density of the catalyst support is between 600 and 800 kg/m$^3$.

11. The process of claim 1, wherein the pyridinecarboxylic ester (II) has a boiling point at atmospheric pressure that is more than 20 higher than the boiling point of the acetylpyridine (I).

12. The process of claim 1, wherein the reaction temperature is between 350 and 450° C.

13. The process of claim 1, wherein the weight ratio of alumina to silica in the catalyst support is between 70:30 and 90:10.

14. The process of claim 1, wherein the weight ratio of alumina to silica in the catalyst support is between 75:25 and 85:15.

15. The process of claim 1, wherein the apparent porosity of the catalyst support is between 60 and 70 percent.

16. The process of claim 1, wherein the packing density of the catalyst support is between 600 and 1000 kg/m$^3$.

17. The process of claim 1, wherein the packing density of the catalyst support system is between 600 and 800 kg/m$^3$.

18. The process of claim 1, wherein the titanium dioxide content of the catalyst is 5 to 20 wt. percent, based on the weight of the support.

* * * * *